(12) United States Patent
Yamada (10) Patent No.: US 12,109,360 B2
(45) Date of Patent: Oct. 8, 2024

(54) TRACHEAL TUBE

(71) Applicant: DAIKEN MEDICAL CO., LTD., Osaka (JP)

(72) Inventor: Masayuki Yamada, Osaka (JP)

(73) Assignee: DAIKEN MEDICAL CO., LTD., Osaka (JP)

( * ) Notice: Subject to any disclaimer, the term of this patent is extended or adjusted under 35 U.S.C. 154(b) by 689 days.

(21) Appl. No.: 16/977,976

(22) PCT Filed: Feb. 27, 2019

(86) PCT No.: PCT/JP2019/007423
§ 371 (c)(1),
(2) Date: Sep. 3, 2020

(87) PCT Pub. No.: WO2019/172029
PCT Pub. Date: Sep. 12, 2019

(65) Prior Publication Data
US 2021/0052840 A1  Feb. 25, 2021

(30) Foreign Application Priority Data
Mar. 7, 2018 (JP) ................................ 2018-040923

(51) Int. Cl.
*A61M 16/04* (2006.01)
(52) U.S. Cl.
CPC ... *A61M 16/045* (2014.02); *A61M 2210/1032* (2013.01); *A61M 2210/1035* (2013.01)
(58) Field of Classification Search
CPC .......... A61M 16/0404; A61M 16/0445; A61M 16/045; A61M 16/0475; A61M 16/0486;
(Continued)

(56) References Cited

U.S. PATENT DOCUMENTS 4,248,221 A * 2/1981 Winnard ........... A61M 16/0404
128/207.15
5,315,992 A * 5/1994 Dalton ............... A61M 16/0486
128/207.14
(Continued)

FOREIGN PATENT DOCUMENTS

| JP | 2002-505925 A | 2/2002 |
|----|---------------|--------|
| JP | 2003-500085 A | 1/2003 |
| JP | 2014-523326 A | 9/2014 |

OTHER PUBLICATIONS

English Translation of International Search Report from PCT/JP2109/007423 dated Apr. 9, 2019.

*Primary Examiner* — Colin W Stuart
*Assistant Examiner* — Matthew D Ziegler
(74) *Attorney, Agent, or Firm* — Calfee, Halter & Griswold LLP (57) ABSTRACT

A tracheal tube can be easily positioned and has no risk of unexpectedly blocking a bronchus. This tracheal tube is inserted through the trachea and a bronchus of a subject, and includes: a tube body which has a through hole formed on the outer peripheral surface; and bronchus cuffs which are formed on the outer peripheral surface of the tube body and which press the inner peripheral surface of the bronchus. The bronchus cuffs are formed spaced apart in the axial direction of the tube body and form a plurality of vent spaces which communicate with each other. The through hole communicates with the vent spaces.

5 Claims, 9 Drawing Sheets (58) Field of Classification Search
CPC .. A61M 2210/1032; A61M 2210/1035; A61M 16/0434–0459
See application file for complete search history.

(56) References Cited

U.S. PATENT DOCUMENTS

| | | | |
|---|---|---|---|
| 5,554,119 A * | 9/1996 | Harrison | A61M 25/1002 |
| | | | 604/101.05 |
| 5,660,175 A | 8/1997 | Dayal | |
| 6,390,988 B1 | 5/2002 | Robinson | |
| 6,550,475 B1 | 4/2003 | Oldfield | |
| 9,526,856 B2 * | 12/2016 | Azagury | A61M 16/0434 |
| 9,687,621 B2 | 6/2017 | Hoftman et al. | |
| 10,071,212 B1 * | 9/2018 | Riesberg | A61M 16/0497 |
| 2003/0040678 A1 | 2/2003 | Robinson et al. | |
| 2013/0158351 A1 | 6/2013 | Daher et al. | |
| 2014/0031622 A1 | 1/2014 | Daher | |
| 2020/0306474 A1 * | 10/2020 | Flaherty | A61F 5/56 |

\* cited by examiner

FIG.9a　　　FIG. 9b　　　FIG. 9c

TRACHEAL TUBE

CROSS-REFERENCE TO RELATED APPLICATIONS

This application is a 371 of PCT Application No. PCT/JP2019/007423 filed on Feb. 27, 2019, which claims priority to Japanese Application No. 2018-040923, filed on Mar. 7, 2018, the contents of which are hereby incorporated by reference as if recited in their entirety.

TECHNICAL FIELD

The present invention relates to a tube inserted into the trachea and bronchi of a subject such as a patient. More specifically, the present invention relates to a tracheal tube in which a cuff is provided on the outer peripheral surface of the tube.

BACKGROUND ART

Conventionally, deformable, flexible tubes have been widely used to adequately control and maintain a subject's breathing conditions when performing surgical procedures on the respiratory system.

Usually, a balloon-like member called a cuff is provided on the outer peripheral surface of such a tube. Further, the cuff communicates with a pore separately provided with the tube. The cuff is inflated and deflated freely by controlling the inflow and outflow of a working fluid, such as air, from the pores into the cuff.

A user, such as a physician, inserts the tracheal tube configured as described above into the trachea of a subject, and inflates the cuff to bring the outer surface of the cuff into close contact with the inner circumferential surface of the trachea of the subject. This ensures that the position of the cuff and tube are fixed. In addition, by ensuring airtightness of the airway, aspiration and gas leakage of the subject can be prevented.

As an invention relating to a tracheal tube, for example, Patent Document 1 describes a tracheal tube in which two cuffs are provided at spaced positions on an outer peripheral surface of a tube. A side hole is provided between the two cuffs on the outer circumferential surface of the tube.

CITATION LIST

Patent Literature

Patent Literature 1: Japanese Translation of PCT International Application Publication No. JP-T-2002-505925

SUMMARY OF INVENTION

Technical Problem

In addition, when separate lung ventilation is performed using such a tracheal tube, a tracheal tube called a double lumen tube (hereinafter referred to as DLT) is frequently used.

The DLT has a structure in which a tracheal tube and a bronchial tube are bonded to each other. Tracheal cuffs and bronchial cuffs are also provided on the outer circumferential surface of the tube at spaced intervals, and inflation and deflation of each cuff is independently controlled.

The user can make a state of a single lung ventilation condition by inserting the tracheal tube over the tracheal bifurcation, the bronchial tube up to the bronchus, and inflating each cuff. In this case, the cuff must be secured in place using a bronchoscope or the like.

Incidentally, the diameter and total length of the human trachea are different between the right main bronchus and the left main bronchus, and the branch distance to the lobe bronchus is also different. For this reason, there are DLTs for the left and for the right.

Normally, regardless of the site to be treated, a DLT for left in which a bronchial tube is inserted into the left main bronchus is used. This is due to a shorter bifurcation distance to the upper lobe bronchus in the right main bronchus compared to the left main bronchus. That is, the right DLT may occlude the right upper lobe bronchus by moving the tracheal tube after inflating the bronchial cuff.

However, anatomically, bronchial tubes tend to enter the right main bronchus and not the left main bronchus. In addition, when a treatment such as total left lung extraction is performed, or when a lesion is present in the left main bronchus, a right DLT is used. For this reason, there has been a great need for the development of a DLT for the right in order to simplify the positioning of the cuff and prevent detachment from the bronchus by the movement of the tracheal tube and bronchial upper lobe occluding by the cuff.

In this regard, even if a through hole as in the invention described in Patent Document 1 is provided in the DLT for right, it is necessary to fix this through hole in accordance with the right upper lobe bronchus. Here, since the positioning of the DLT is a delicate work for confirming the depth and position using the bronchoscope, accurate positioning becomes difficult. In particular, when the body position of the subject is changed in order to secure the operative field, the cuff is moved from a position where the cuff is fixed at one end by an external force, which hinders smooth operation.

It is an object of the present invention to provide a tracheal tube which can be easily positioned and which is not liable to occlude the bronchus unexpectedly.

Solution to Problem

In order to solve the above problems, a tracheal tube inserted through the trachea and bronchi of a subject, comprising: a tube body having a through hole on an outer circumferential surface thereof, a bronchial cuff provided on an outer circumferential surface of the tube body and pressing an inner circumferential surface of the bronchus;

wherein the bronchial cuff is spaced apart in the axial direction of the tube body and forms a plurality of ventilation spaces;

wherein the ventilation spaces are in communication with each other;

wherein the through hole communicate with the ventilation space.

According to the present invention, the lobar bronchus can be made to be in a ventilatable state by communicating the lobar bronchus with any of a plurality of ventilation spaces communicating with each other. That is, it is unnecessary to perform positioning in consideration of the position of the through hole strictly. In addition, since the bronchial cuffs are provided on both axial sides of each ventilation space, a high frictional force is ensured between the bronchi and the tube body.

According to a preferred embodiment of the present invention, the bronchial cuff is formed into a continuous helical shape.

With such a configuration, the contact area between the inner peripheral surface of the bronchus and the outer peripheral surface of the bronchial cuff is increased, and the frictional force between the bronchus and the bronchial cuff is improved. That is, it becomes possible to more firmly fix the present invention to the trachea and bronchi of the subject.

Also, since only one pore is used to control inflation and deflation of the bronchial cuff, the maneuverability and manufacturability of the tracheal tube itself are improved.

Further, the helical shape makes it possible to form a continuous ventilation space.

According to a preferred embodiment of the present invention, at least one of the upper or lower portions of the bronchial cuff is provided with a sealing cuff for ensuring airtightness.

With such a configuration, it is possible to secure high airtightness between the inner peripheral surface of the bronchus and the outer peripheral surface of the tube body.

According to a preferred embodiment of the present invention, a tracheal cuff for pressing the inner peripheral surface of the trachea is provided on the outer peripheral surface of the tube body.

With such a configuration, the space between the inner peripheral surface of the trachea and the outer peripheral surface of the tube body can be sealed. This makes it possible for the user to temporarily stop the movement of either the right or left lungs of the subject, and to perform separate lung ventilation.

According to a preferred embodiment of the present invention,

The tube body includes a first path and a second path;

The bronchial cuff is provided on the outer peripheral surface of the first path;

The tracheal cuff is provided on the outer circumferential surfaces of the first path and the second path, The second path have an open end between the bronchial cuff and the tracheal cuff.

With such a configuration, the present invention can be used as a DLT. That is, the user can freely control the introduction of a predetermined fluid such as air into the right and left lungs.

According to a preferred embodiment of the present invention, a plurality of the through holes are provided in the ventilation spaces.

With such a configuration, it is possible to improve the air permeability between the lobar bronchus and the outside air.

According to a preferred embodiment of the present invention, the width of the bronchial cuff in the inflated state is smaller than the inner diameter of the lobular bronchus.

With such a configuration, even when the fixing position of the present invention is changed, it is possible to prevent the lobar bronchus from being unintentionally occluded by the bronchial cuff.

According to a preferred embodiment of the present invention, in the inflated state of the bronchial cuff, an axial interval of the ventilation spaces is larger than an inner diameter of the lobular bronchus.

With such a configuration, it is possible to form a large through hole and to improve air permeability between the leaf bronchus and the outside air.

Advantageous Effects of Invention

According to the present invention, it is possible to provide a tracheal tube which can be easily positioned and which is not liable to occlude the bronchus unexpectedly.

BRIEF DESCRIPTION OF DRAWINGS

FIG. 7($a$) and ($b$) are partially enlarged perspective views showing a modification of the tracheal tube according to an embodiment of the present invention.

FIG. 9($a$)-($b$) are partially enlarged perspective views showing a modification of the tracheal tube according to an embodiment of the present invention.

DESCRIPTION OF EMBODIMENTS

Hereinafter, a tracheal tube according to an embodiment of the present invention will be described with reference to FIGS. 1 to 6. Note that the embodiment described below is an example of the present invention, and the present invention is not limited to the following embodiments.

Note that, in these drawings, reference numeral 1 denotes a tracheal tube according to the present embodiment.

Figure 1:
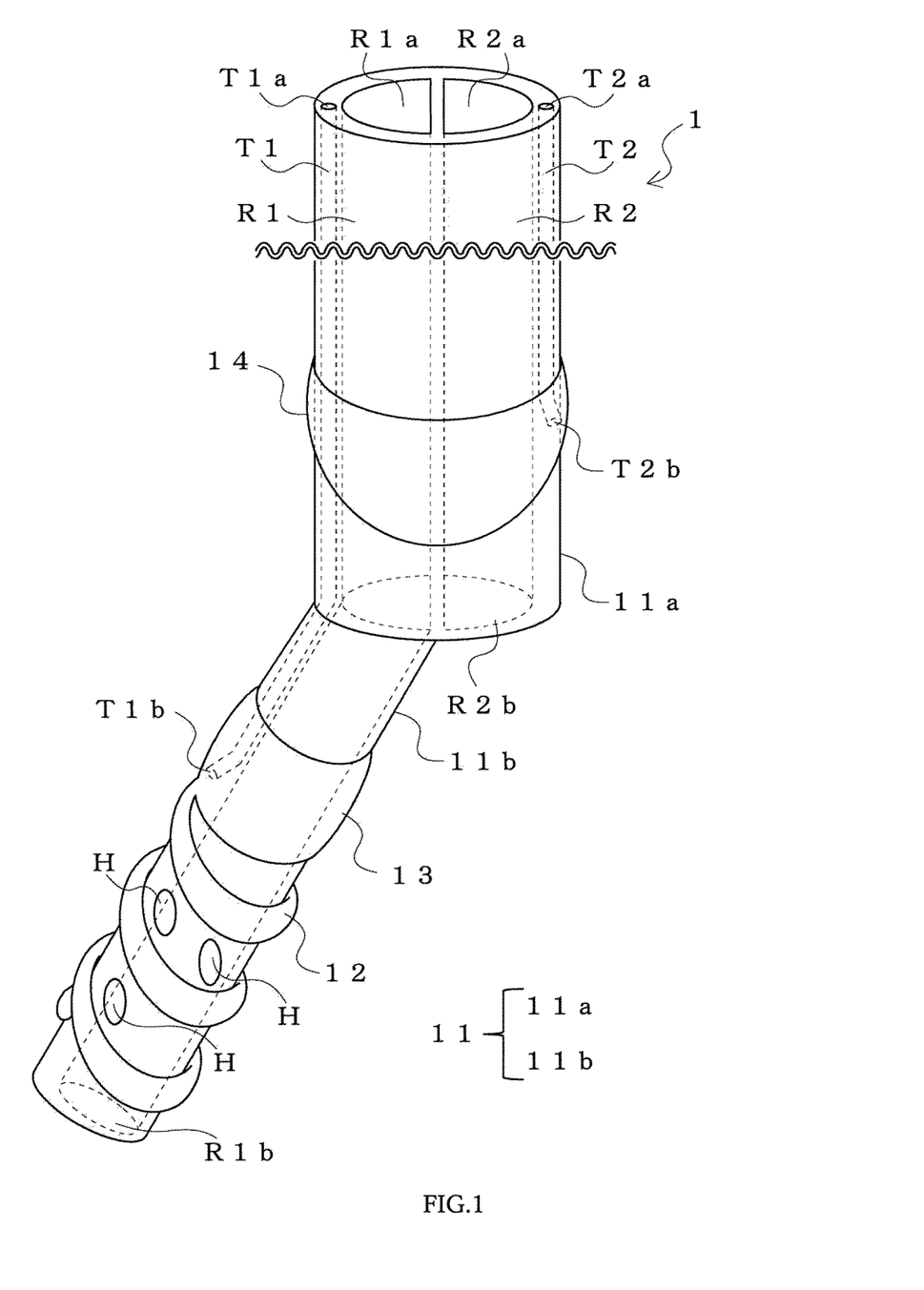
FIG. 1 is a schematic perspective view of a tracheal tube according to an embodiment of the present invention.

As shown in FIG. 1, the tracheal tube 1 comprises a tube body 11, a bronchial cuff 12, a sealed cuff 13, and a tracheal cuff 14.

Note that the shapes of the first path R1, the second path R2, the first pore T1, and the second pore T2, which will be described later, inside the tube main body 11 are indicated by dotted lines.

The tube body 11 includes a main tube 11$a$ inserted to the trachea of the subject and a branch tube 11$b$ inserted to the bronchus of the subject.

Inside the main tube 11$a$, a first path R1 and a second path R2 are formed.

Inside the branch tube 11$b$, a first path R1 is formed to extend from the first path R1 of the main tube 11$a$. A plurality of through holes H are formed in the outer peripheral surface of the branch tube 11$b$.

An inflow opening end R1$a$ of the first path R1 and an inflow opening end R2$a$ of the second path R2 are formed above the main tube 11$a$. The inflow opening ends R1$a$ and R2$a$ are connected to a device (not shown) via an adapter (not shown), whereby a predetermined fluid such as air is introduced into the first path R1 and the second path R2.

The outflow opening end R1$b$ of the first path R1 is formed at the end of the branch tube 11$b$. The outflow opening end R2$b$ of the second path R2 is formed at a connecting portion between the main tube 11$a$ and the branch tube 11$b$.

By connecting a device (not shown) to the inflow opening ends R1a and R2a via an adapter (not shown), the user can freely control the introduction of a predetermined fluid such as air into each path.

Inside the main tube 11a and the branch tube 11b, a first pore T1 for supplying a predetermined fluid such as air to the bronchial cuff 12 and the sealed cuff 13 is provided along the tube walls of the main tube 11a and the branch tube 11b. Then, the outflow opening end T1b of the first pore T1 is formed inside the sealed cuff 13

Further, inside the main tube 11a, a second pore T2 for supplying a predetermined fluid such as air to the tracheal cuff 14 is provided along the tube wall of the main tube 11a. The outflow opening end T2b of the second pore T2 is formed inside the tracheal cuff 14.

The inflow opening end T1a of the first pore T1 and the inflow opening end T2a of the second pore T2 are connected to, for example, a pilot balloon (not shown) having a valve mechanism or the like. By this pilot balloon or the like, a predetermined fluid such as air is supplied to the bronchial cuff 12, the sealed cuff 13, and the tracheal cuff 14 via the first pore T1 and the second pore T2

Although there is no particular limitation on the material of the tube body 11, for example, the following flexible polymeric materials are preferably used.

A polyamide resin or polyamide elastomer such as nylon 11, nylon 12, nylon 610, polyolefin such as polypropylene or polyethylene, olefin elastomer such as polyethylene elastomer or polypropylene elastomer, polyester such as polyethylene terephthalate, soft polyvinyl chloride, polyurethane or polyurethane elastomer, fluororesin such as polytetrafluoroethylene and fluororesin elastomer, polyimide, ethylene-vinyl acetate copolymer, silicone rubber.

One or two or more of these can also be used in combination.

By being formed of such a material, the tube body 11 has appropriate flexibility and self-sustaining property.

The bronchial cuff 12 and the sealing cuff 13 are provided on the outer peripheral surface of the branch tube 11b.

The tracheal cuff 14 is provided on the outer peripheral surface of the main tube 11a.

Note that the attachment of each cuff to the outer peripheral surface of the tube body 11 is performed by an adhesive or heat fusion or the like, but is not particularly limited.

The bronchial cuff 12, the sealed cuff 13, and the tracheal cuff 14 are composed of a cylindrical membrane member by various kinds of polymer materials (particularly, thermoplastic resins). Each cuff is preferably constructed of a material that is flexible as a whole.

As a material for each cuff, for example, the following materials are preferably used. A polyamide resin or a polyamide elastomer such as nylon 11, nylon 12, or nylon 610, a polyester such as polyethylene terephthalate (PET), a natural rubber, polypropylene, polyethylene, ethylene-propylene, a copolymer, a polyolefin such as an ethylene-vinyl acetate copolymer, a soft polyvinyl chloride, a polyurethane, a polyisoprene, a polyimide, a polyimide elastomer, a polytetrafluoroethylene, a silicone, or a polymer blend containing at least one of them, a polymer alloy, and the like.

By being formed of such a material, each cuff is prevented from being pushed back by a reaction force from the inner peripheral surface of the trachea or the bronchus at the time of inflation.

Figure 2:
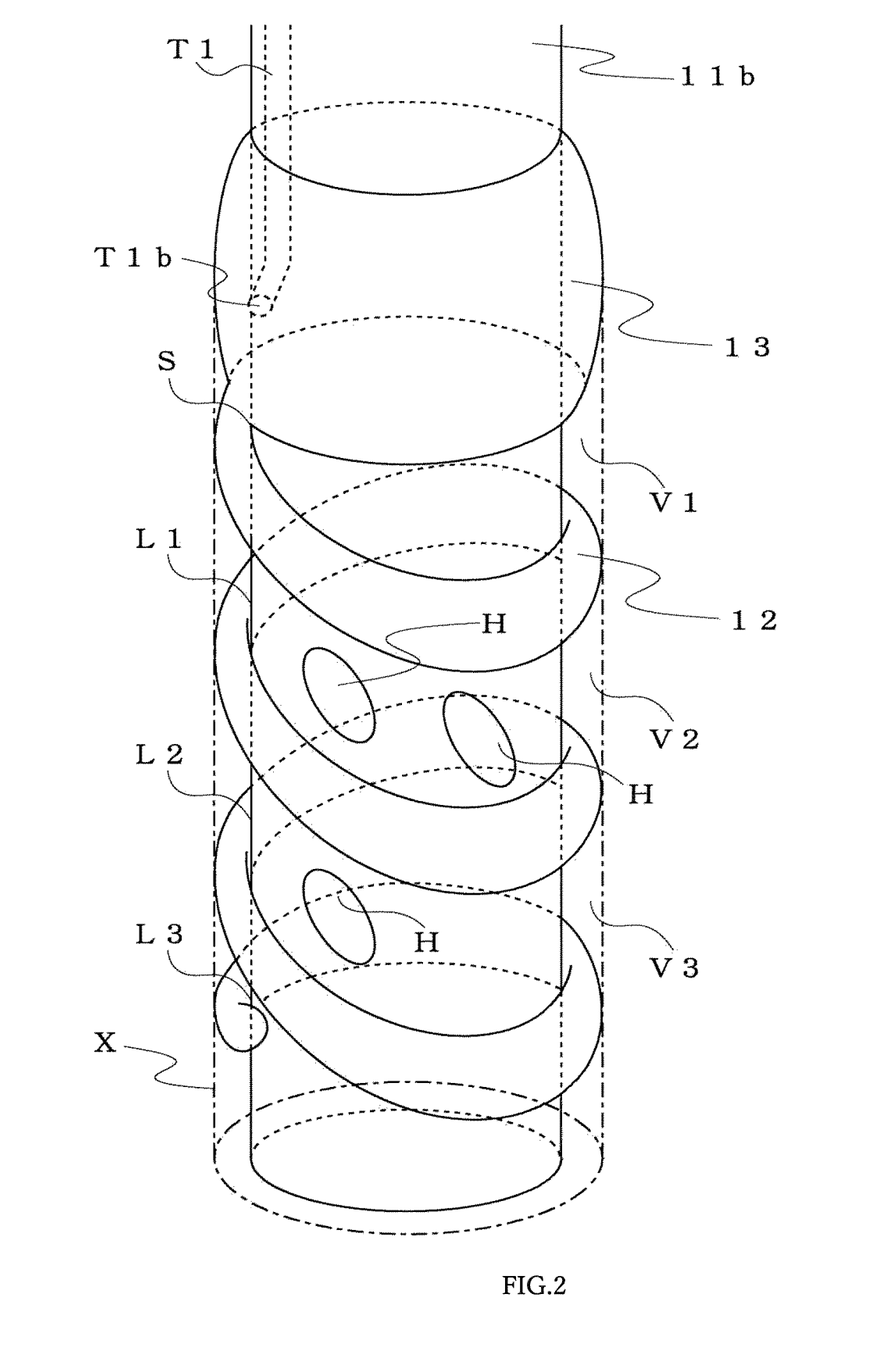
FIG. 2 is a partially enlarged perspective view of a tracheal tube according to an embodiment of the present invention.

FIG. 2 is an enlarged perspective view of the branch tube 11b in FIG. 1.

Note that the hidden line is indicated by a dotted line, but the first path R1 is omitted.

As shown in FIG. 2, the bronchial cuff 12 has an elongated shape having a constant outer diameter and an inner diameter, and is provided in a helical shape at a constant interval in the axial direction of the branch tube 11b. The sealing cuff 13 is provided above the bronchial cuff 12 so as to be integral with the bronchial cuff 12. The interior of the sealing cuff 13 communicates with the interior of the bronchial cuff 12.

Note that the bronchial cuff 12 and the sealed cuff 13 may be formed separately. At this time, by providing the pores corresponding to the bronchial cuff 12 and the sealed cuff 13 respectively, the user can independently control the inflation and deflation of the bronchial cuff 12 and the sealed cuff 13

Here, a surface of the outer peripheral surface of the branch tube 11b on which the bronchial cuff 12 does not overlap is referred to as an exposed surface. Then, above the branch tube 11b, the point S where the exposed surface starts to appear is referred to as an exposed surface forming start point S. Further, the outer contour line L1 of the branch tube 11b when rotated 360 degrees in the spiral direction from the exposed surface forming start point S is referred to as an exposed line L1, the outer contour line L2 of the branch tube 11b when rotated 360 degrees in the spiral direction from the exposed line L1 is referred to as an exposed line L2, and the outer contour line L3 of the branch tube 11b when rotated 360 degrees from the exposed line L2 is referred to as an exposed line L3.

Next, when an imaginary cylindrical body X in which the outer peripheral surface of the bronchial cuff 12 abuts is assumed, a space between the inner peripheral surface and the exposed surface of the cylindrical body X is closed. Then, in this closed space, the space exposed surface from the exposed surface forming start point S to the exposed line L1 is included is referred to as an ventilation space V1, the space exposed surface from the exposure line L1 to the exposure line L2 is included is referred to as an ventilation space V2, the space exposed surface from the exposed line L2 to the exposed line L3 is included is referred to as an ventilation space V3.

Note that the cylindrical body X can be replaced with, for example, a right main bronchus WR or a left main bronchus WL of the subject, which will be described later.

Since the bronchial cuff 12 is provided in a helical shape, the ventilation spaces V1, V2, and V3 communicate with each other.

The number of ventilation spaces is not particularly limited, and can be arbitrarily increased by increasing the number of turns of the bronchial cuff 12 on the outer circumferential surface of the branch tube 11b.

The two through holes H communicate with the ventilation space V2 and The one through hole H communicates with the ventilation space V3.

The number of through holes H is not particularly limited, and may be communicated only one to the ventilation space V1, for example, or may be communicated with each of the ventilation spaces 3 or more.

An example of the use of the tracheal tube 1 will be described below with reference to FIGS. 3 to 6.

Figure 3:
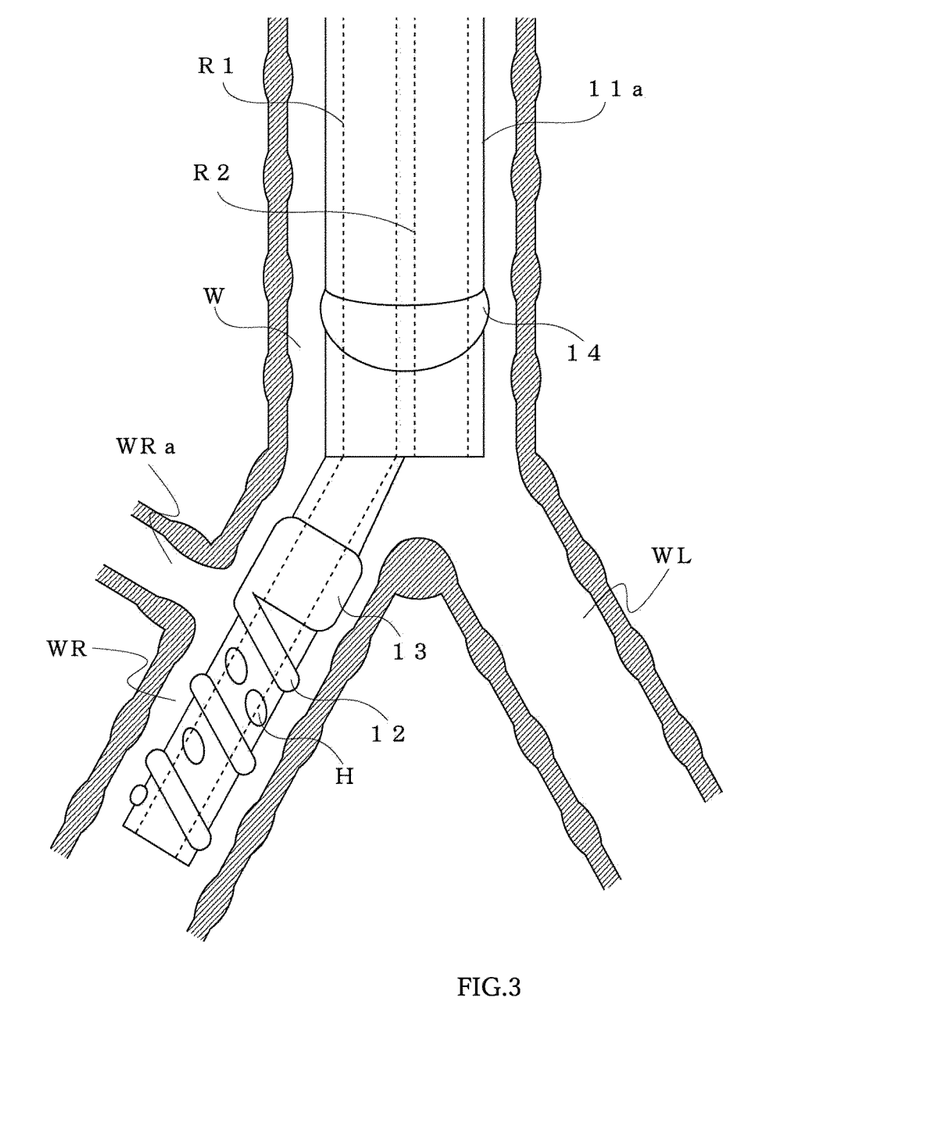
FIG. 3 is a front view showing an example of use of a tracheal tube according to an embodiment of the present invention.

First, as shown in FIG. 3, the user inserts the tracheal tube 1 into the trachea W and the right main bronchus WR of the subject with each cuff in a deflated state. More specifically, the main tube 11a is inserted into the trachea W, and the branch tube 11b passes through the trachea W and is inserted into the right main bronchus WR.

Figure 4:
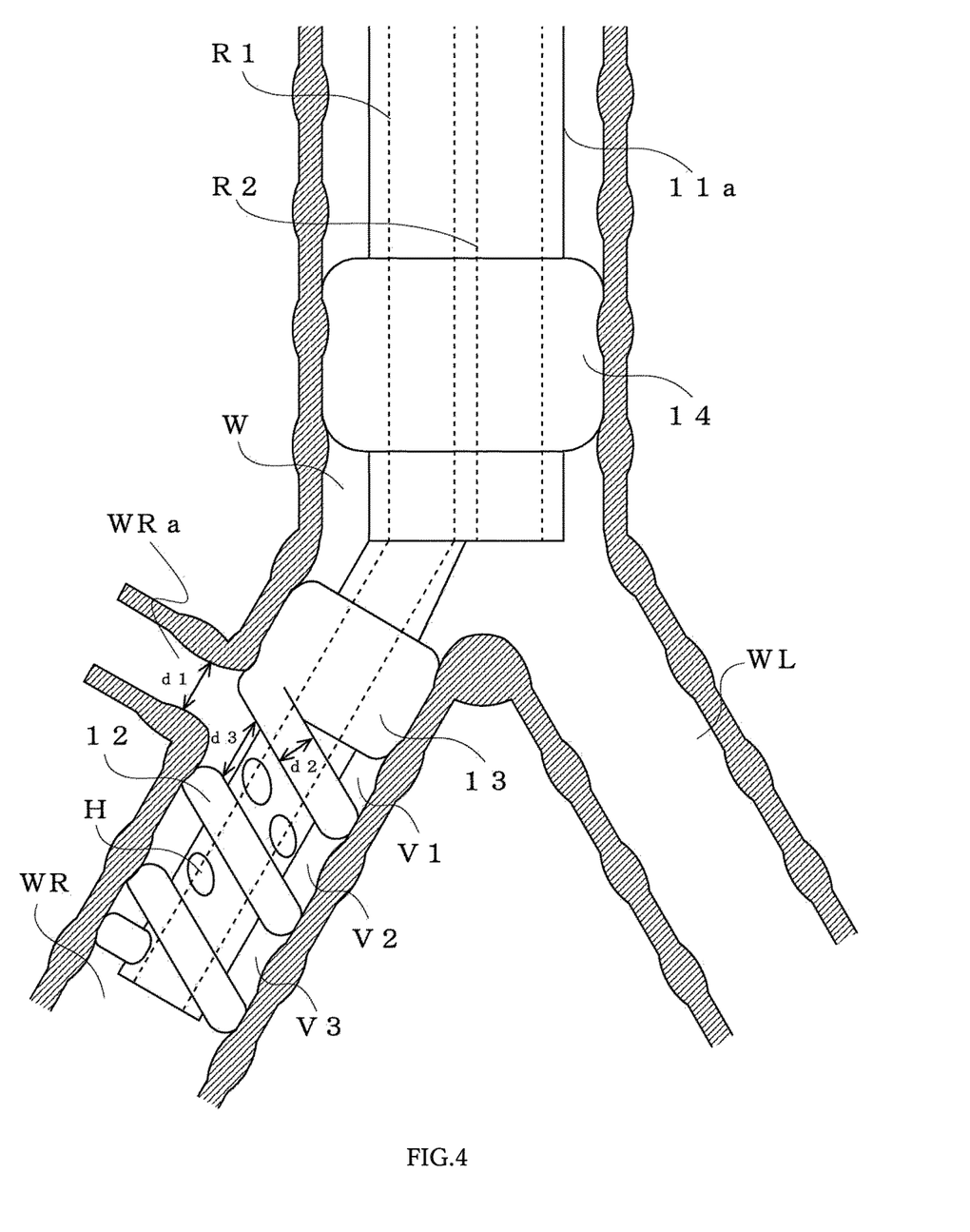
FIG. 4 is a front view showing an example of use of a tracheal tube according to an embodiment of the present invention.

Next, as shown in FIG. 4, the user inflates the bronchial cuff 12, the sealed cuff 13 and the tracheal cuff 14 via the first pore T1 and the second pore T2.

Thereby, the tracheal cuff 14 presses the inner peripheral surface of the trachea W, and the space between the inner peripheral surface of the trachea W and the outer peripheral surface of the main tube 11a is sealed. Then, the left lung of the subject and the outside air are communicated with each other through the second path R2.

The sealing cuff 13 presses the inner peripheral surface of the right main bronchus WR at a position above the right upper lobe bronchus WRa. The bronchial cuff 12 presses the inner peripheral surface of the right main bronchus WR at a position below the right upper lobe bronchus WRa.

As a result, the space between the upper and lower inner peripheral surfaces of the right main bronchus WR with the right upper lobe bronchus WRa interposed therebetween and the outer peripheral surface of the branch tube 11b is sealed. Then, the right lung of the subject and the outside air are communicated with each other through the first path R1. Further, the right main bronchus WR and the right upper lobe bronchus WRa are communicated with each other through the through hole H by the first path R1.

In FIG. 4, the right upper lobe bronchus WRa is communicated with the ventilation spaces V1 and V2. The outer diameter d2 of the bronchial cuffs 12 in the inflated state is smaller than the inner diameter d1 of the right upper lobe bronchus WRa. Further, in the inflated state of the bronchial cuff 12, the axial distance d3 of the ventilation space V2 is configured to be larger than the inner diameter d1 of the right upper lobe bronchus WRa.

Note that since the inner diameter of the right upper lobe bronchus WRa of an adult is usually about 6 mm to 7 mm, it is preferable that the outer diameter d2 is less than 6 mm and the distance d3 is not less than (d2/4) mm.

Figure 5A:
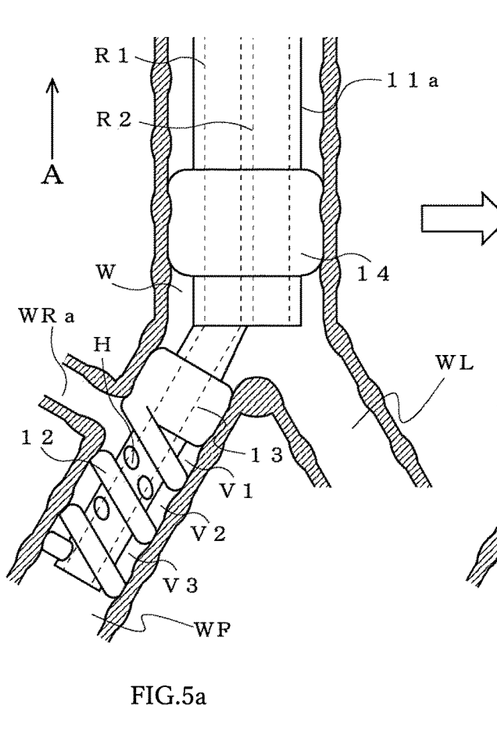
FIG. 5 is a front view showing an example of use of a tracheal tube according to an embodiment of the present invention.
Figure 5B:
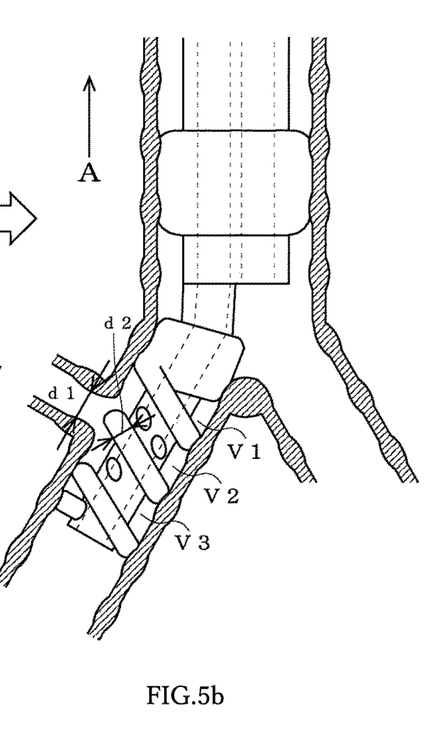

With reference to FIG. 5, a case in which the body position of the subject changes from a state in which the tracheal tube 1 is positioned at a predetermined position, or a case in which an external force acts directly on the tracheal tube 1 will be described.

Note that, the case where the external force directly acts on the tracheal tube 1 includes, for example, a case where the shape of the bronchus is deformed by body position change, a case where the elastic force of the tube main body 11 acts, a case where the tracheal tube 1 is pulled by the weight of the corrugated tube, or the like. In these cases, the tracheal tube 1 may move towards the subject's mouth.

As shown in FIG. 5, it is assumed that the tracheal tube 1 has moved from the state shown in FIG. 4 to the mouth side (direction of arrow A) of the subject (from the left view to the right view of FIG. 5).

At this time, since the outer diameter d2 of the bronchial cuff 12 in the inflated state is smaller than the inner diameter d1 of the right upper lobe bronchus WRa, the bronchial cuff 12 does not occlude the right upper lobe bronchus WRa.

At this time, the right upper lobe bronchus WRa is communicated with the ventilation spaces V1, V2, and V3.

Figure 6A:
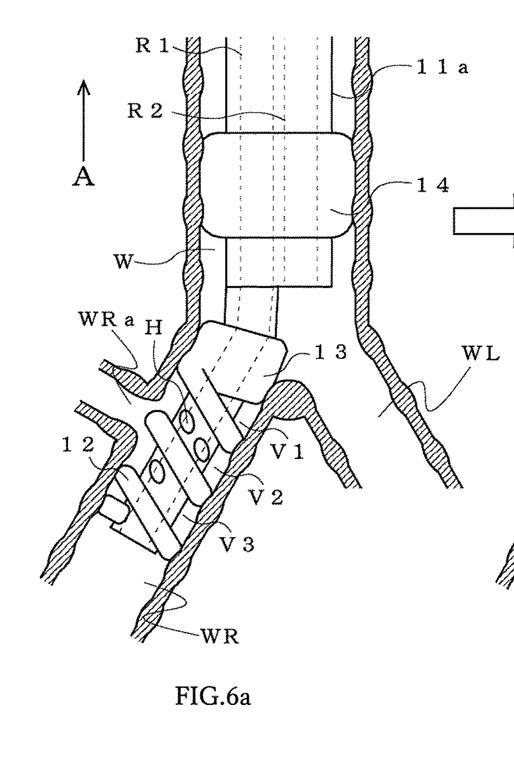
FIG. 6 is a front view showing an example of use of a tracheal tube according to an embodiment of the present invention.
Figure 6B:
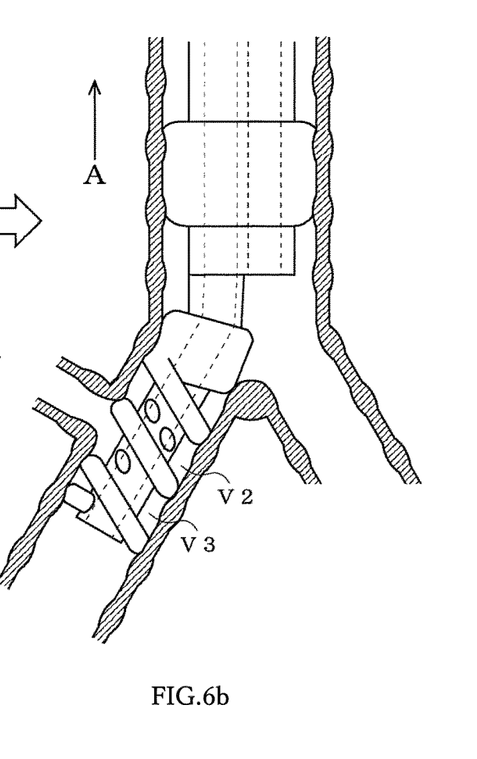

As shown in FIG. 6, it is assumed that the tracheal tube 1 has moved from the state shown in the right view of FIG. 5 to the mouth side (direction of arrow A) of the subject (from the left view to the right view of FIG. 6).

At this time, the right upper lobe bronchus WRa is communicated with the ventilation spaces V2 and V3.

As described above, according to the present embodiment, even when the tracheal tube 1 is moved, the right upper lobe bronchus WRa is always communicated with any of the ventilation spaces V1, V2, and V3, so that there is no risk of unintentionally occluding the right upper lobe bronchus WRa.

When the tracheal tube 1 is inserted, if any of the ventilation spaces V1, V2, and V3 is communicated with the right upper lobe bronchus WRa, the right upper lobe bronchus WRa can be brought into a ventilating state. That is, labor for positioning is unnecessary in consideration of the position of the through hole H strictly.

Further, since the bronchial cuff 12 or the sealing cuff 13 is provided on both axial sides of each ventilation space, a high frictional force is ensured between the right main bronchus WR and the branch tube 11b.

In addition, since the bronchial cuff 12 is formed in a continuous helical shape, the contact area between the inner peripheral surface of the right main bronchus WR and the outer peripheral surface of the bronchial cuff 12 increases, and the frictional force between the right main bronchus WR and the bronchial cuff 12 improves. That is, the tracheal tube 1 can be more firmly fixed to the trachea W and the right main bronchus WR of the subject.

Furthermore, since only one pore is provided for controlling the inflation and deflation of the bronchial cuff 12, the operability and manufacturability of the tracheal tube 1 are improved.

Further, since the sealing cuff 13 for ensuring airtightness is provided above the bronchial cuff 12, high airtightness between the inner peripheral surface of the right main bronchus WR and the outer peripheral surface of the branch tube 11b can be ensured.

In addition, since the tracheal cuff 14 for pressing the inner peripheral surface of the trachea W is provided on the outer peripheral surface of the main tube 11a, the space between the inner peripheral surface of the trachea W and the outer peripheral surface of the main tube 11a can be sealed. This makes it possible for the user to temporarily stop the movement of either the right or left lungs of the subject, and to perform separate lung ventilation.

The tracheal tube 1 is a DLT, and the user can freely control the introduction of a predetermined fluid such as air into the right and left lungs.

In addition, since the outer diameter d2 of the bronchial cuff 12 in the inflated state is configured to be smaller than the inner diameter d1 of the right upper lobe bronchus WRa, even when the fixing position of the tracheal tube 1 is changed, it is possible to prevent the lobe bronchus from being accidentally occluded by the bronchial cuff 12.

Further, since the distance d3 in the axial direction of the ventilation spaces V1, V2, and V3 is configured to be larger than the inner diameter d1 of the right upper lobe bronchus WRa, the through hole H can be formed to be large, and the breathability between the right upper lobe bronchus WRa and the outside air can be improved.

It should be noted that the shapes, dimensions, and the like of the constituent members described in the above embodiment are examples, and can be variously changed based on design requirements and the like.

Figure 7A:
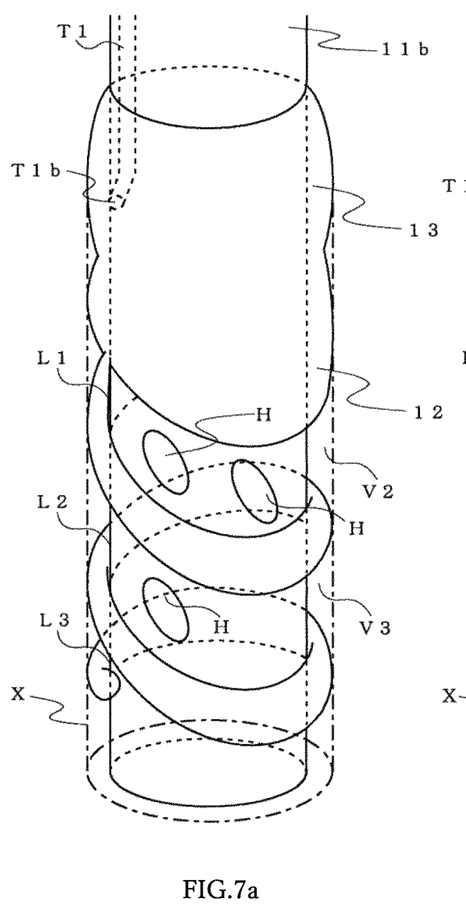

For example, as shown in FIG. 7a, the sealed cuff 13 may be formed by integrally molding with the upper portion of the bronchial cuff 12 so as to fill the ventilation space V1 shown in FIG. 2.

Figure 7B:
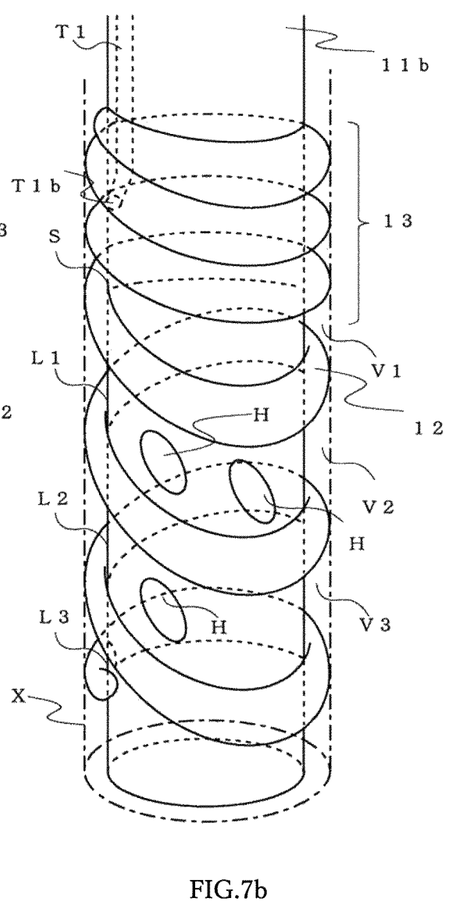

Further, as shown in FIG. 7b, the sealed cuff 13 may be formed by helically winding the bronchial cuff 12 upward with no gap around the branch tube 11b.

Figure 8:
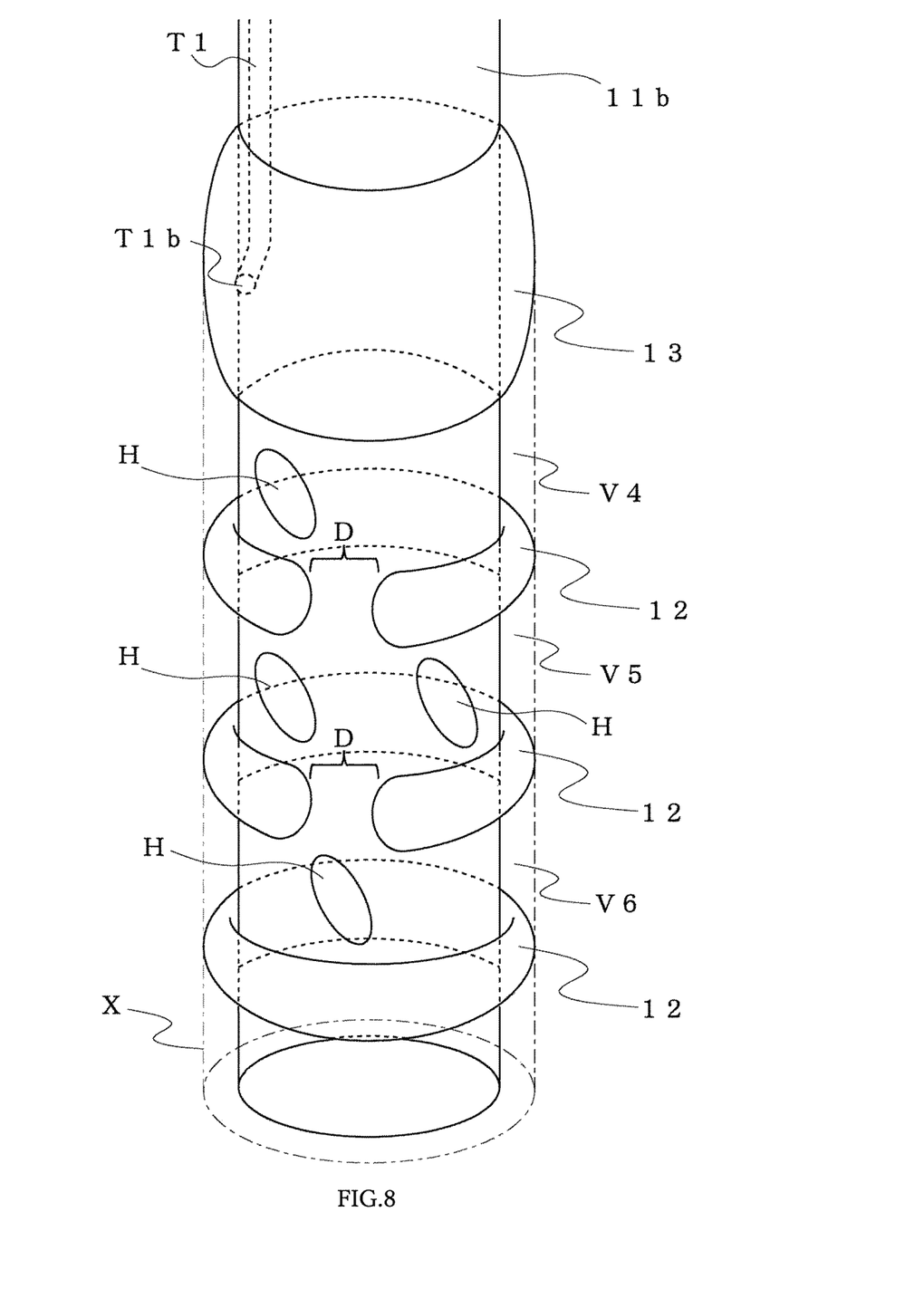
FIG. 8 is a partially enlarged perspective view showing a modification of the tracheal tube according to an embodiment of the present invention.

Further, as shown in FIG. 8, a plurality of annular bronchial cuffs 12 (three in FIG. 7) may be provided at intervals. In this manner, the spaces between the sealing cuff 13 and each bronchial cuff 12 become the ventilation spaces V4, V5, V6.

In such a configuration, the discontinuity D is formed in the bronchial cuff 12 provided between the sealing cuff 13 and the lowermost bronchial cuff 12. By doing so, the ventilation spaces V4, V5 and V6 communicate with each other, and substantially the same effect as that of the tracheal tube 1 shown in FIGS. 1 to 6 can be achieved.

Note that, in FIG. 8, pores corresponding to the plurality of bronchial cuffs 12 are omitted.

Figure 9A:
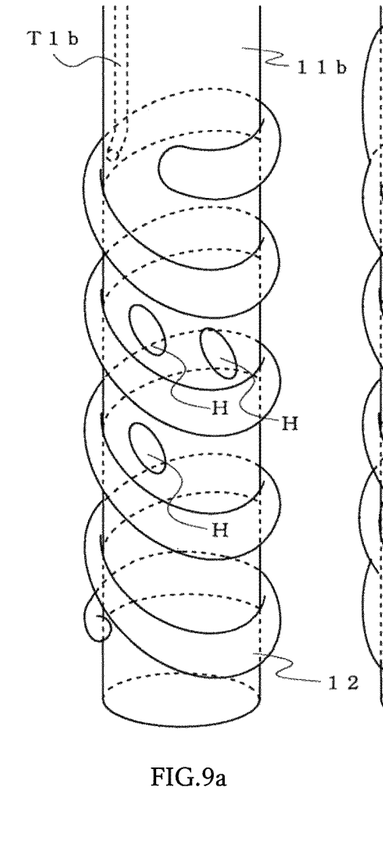

Further, as shown in FIG. 9a, a configuration may be employed in which the sealing cuff 13 is not provided in the branch tube and only the bronchial cuff 12 is provided.

Figures 9B, 9C:
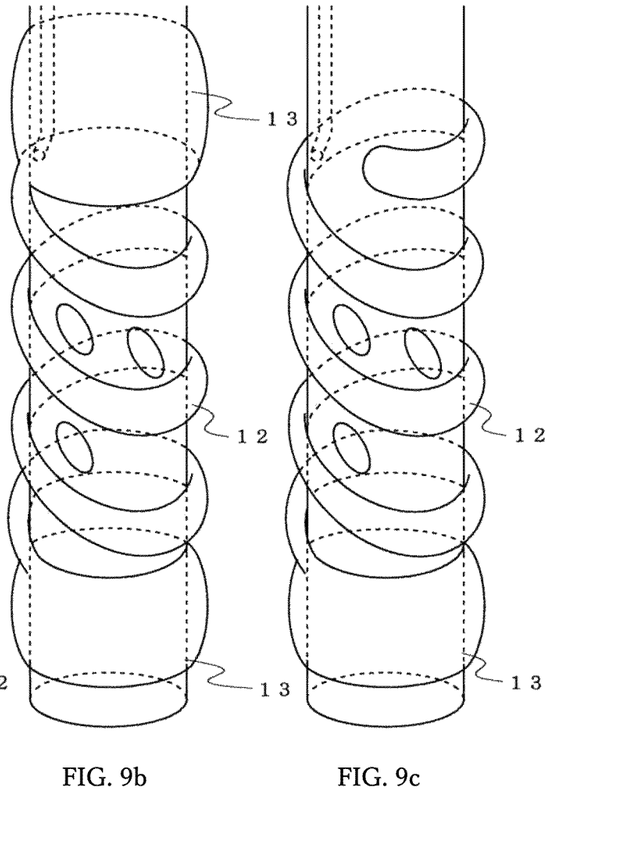

In addition, as shown in FIG. 9b, the sealing cuff 13 may be provided at both of the main tube 11a side end and the outflow opening end R1b side end of the bronchial cuff 12.

Further, as shown in FIG. 9c, the sealing cuff 13 may be provided only at the outflow opening end R1b side end of the bronchial cuff 12.

In FIGS. 7 to 9, the hidden line is indicated by a dotted line, but the first path R1 is omitted.

Also, the present invention is applicable to all tubes used when performing a surgical procedure using a cuff capable of inflating and deflating. That is, the present invention is applicable to all tubes used for the treatment to not only the trachea and bronchi, but also treat body lumens such as blood vessels, bile ducts, esophagus, airways, urethra and other organs, or body cavities.

INDUSTRIAL APPLICABILITY

Thus, the present invention has extremely high industrial applicability because it can be positioned easily and there is no risk of abruptly occluding the bronchus when performing a surgical operation on the respiratory system such as separate lung ventilation.

REFERENCE SIGNS LIST

1 Tracheal tube
11 Tube body
11a Main tube
11b Branch tube
12 Bronchial cuff
13 Sealed cuff
14 Tracheal cuff
R1 First path
R2 Second path
T1 First pore
T2 Second pore
H Through hole
W Trachea
WR Bronchus principalis dexter
WRa Right upper lobe bronchus
WL Bronchus principalis sinister
X Cylindrical body
D Discontinuity
V1, V2, V3, V4, V5, V6 Ventilation space

The invention claimed is:

1. A tracheal tube configured to be inserted through the trachea and bronchi of a subject, comprising: a tube body having a through hole on an outer circumferential surface thereof, a single bronchial cuff provided on the outer circumferential surface of the tube body and configured to be inserted into the main bronchus of the subject and press an inner circumferential surface of the main bronchus;
   wherein the bronchial cuff is a single elongated shape and is provided in a helical shape at a constant interval in the axial direction of the tube body and forms a plurality of ventilation spaces;
   wherein the ventilation spaces are in internal fluid communication with each other and with an outflow opening end and an inflow opening end of the tube body via the through hole;
   wherein the through hole communicates with the ventilation space;
   wherein the width of the outer diameter of the bronchial cuff in the inflated state is smaller than the inner diameter of a lobular bronchus; and
   wherein in the inflated state of the bronchial cuff, an axial interval of the ventilation spaces is larger than an inner diameter of the lobular bronchus such that air permeability is improved between the lobular bronchus and outside air.

2. The tracheal tube according to claim 1, wherein at least one of the upper or lower portions of the bronchial cuff is provided with a sealing cuff for ensuring airtightness.

3. The tracheal tube according to claims 1, wherein a tracheal cuff configured to press an inner peripheral surface of the trachea is provided on an outer peripheral surface of the tube body.

4. The tracheal tube according to claim 3, wherein the tube body has a main tube that is inserted into the trachea of the subject and a branch tube that is inserted into the main bronchus of the subject;
   wherein the main tube has a first path and a second path;
   wherein the first path and the second path are formed inside the main tube;
   wherein the first path is formed in the inside of the branch tube as an extension from the first path of the main tube;
   wherein the inflow opening ends of the first and second path are formed above the main tube;
   wherein the outflow opening end of the first path is formed at the end of the branch tube, and the outflow opening end of the second path is formed at the connecting portion between the main tube and the branch tube;
   the bronchial cuff is provided on the outer peripheral surface of the branch tube;
   the tracheal cuff is provided on the outer circumferential surfaces of the main tube; and
   the second path has an open end between the bronchial cuff and the tracheal cuff.

5. The tracheal tube according to any one of claims 1 and 2-4, wherein a plurality of through holes are provided in the ventilation spaces.

* * * * *